(12) United States Patent
Folske et al.

(10) Patent No.: US 10,306,687 B2
(45) Date of Patent: May 28, 2019

(54) TRANSMITTING ATHLETIC DATA USING NON-CONNECTED STATE OF DISCOVERY SIGNAL

(71) Applicant: NIKE, Inc., Beaverton, OR (US)

(72) Inventors: Keith Folske, Wilsonville, OR (US); Summer Schneider, Portland, OR (US); Rachel Blackman, Seattle, WA (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 15/167,437

(22) Filed: May 27, 2016

(65) Prior Publication Data

US 2016/0353503 A1 Dec. 1, 2016

Related U.S. Application Data

(60) Provisional application No. 62/167,943, filed on May 29, 2015.

(51) Int. Cl.
*H04W 76/14* (2018.01)
*H04W 4/02* (2018.01)
*H04W 8/00* (2009.01)
*G06F 1/16* (2006.01)
*A43B 3/00* (2006.01)

(52) U.S. Cl.
CPC ........... *H04W 76/14* (2018.02); *A43B 3/0005* (2013.01); *G06F 1/163* (2013.01); *H04W 4/023* (2013.01); *H04W 8/005* (2013.01); *A63B 2225/50* (2013.01)

(58) Field of Classification Search
CPC ............... H04W 76/023; H04W 48/10; H04W 4/02–4/025; H04W 76/00–76/28; H04W 8/005
See application file for complete search history.

(56) References Cited

U.S. PATENT DOCUMENTS

| 6,356,856 | B1 | 3/2002 | Damen et al. |
| 7,454,002 | B1 | 11/2008 | Gardner et al. |
| 7,805,149 | B2 | 9/2010 | Werner et al. |
| 7,927,253 | B2 | 4/2011 | Vincent et al. |
| 8,241,184 | B2 | 8/2012 | DiBenedetto et al. |
| 8,312,392 | B2 | 11/2012 | Forutanpour et al. |
| 8,784,115 | B1 | 7/2014 | Chuang |

(Continued)

FOREIGN PATENT DOCUMENTS

| WO | 2015021223 A1 | 2/2015 |
| WO | 20150025619 A1 | 2/2015 |

OTHER PUBLICATIONS

Aug. 29, 2016—(WO) ISR & WO—App. No. PCT/US16/034770.
(Continued)

*Primary Examiner* — Gennadiy Tsvey
(74) *Attorney, Agent, or Firm* — Banner & Witcoff, Ltd.

(57) ABSTRACT

Systems and methods for locating a wireless device in a "noisy environment" is provided. Embodiments relate to locating and wirelessly transmitting signals to a fitness device located proximate to other electronic devices is disclosed. In one embodiment, advertisement tokens and RSSI can be used for signal strength indication and then transmit a specific signal to the device. Examples include imprinting the fitness device to have a unique wireless identifier.

18 Claims, 6 Drawing Sheets

(56) References Cited

U.S. PATENT DOCUMENTS

| | | |
|---|---|---|
| 8,886,118 B2 | 11/2014 | Reuss et al. |
| 8,910,868 B1 | 12/2014 | Wade et al. |
| 9,585,184 B1 * | 2/2017 | Sheriff .................. H04W 76/15 |
| 2003/0114256 A1 | 6/2003 | Mathog |
| 2005/0135306 A1 | 6/2005 | McAllen et al. |
| 2006/0234632 A1 | 10/2006 | Lin et al. |
| 2007/0094658 A1 | 4/2007 | DiCarlo et al. |
| 2007/0260421 A1 | 11/2007 | Berner et al. |
| 2008/0242220 A1 | 10/2008 | Wilson et al. |
| 2008/0320587 A1 | 12/2008 | Vauclair et al. |
| 2010/0020186 A1 | 1/2010 | Matsui |
| 2010/0268806 A1 | 10/2010 | Kumar et al. |
| 2010/0325710 A1 | 12/2010 | Etchegoyen |
| 2011/0275940 A1 | 11/2011 | Nims et al. |
| 2012/0274508 A1 | 11/2012 | Brown et al. |
| 2013/0104120 A1 | 4/2013 | Arrizza et al. |
| 2013/0137943 A1 | 5/2013 | Pinto Rodrigues |
| 2013/0274635 A1 | 10/2013 | Coza et al. |
| 2014/0023049 A1 | 1/2014 | Strecker et al. |
| 2014/0096126 A1 | 4/2014 | Gourlay et al. |
| 2014/0135042 A1 | 5/2014 | Buchheim et al. |
| 2014/0223421 A1 | 8/2014 | Carter et al. |
| 2014/0235166 A1 * | 8/2014 | Molettiere ............... H04B 7/26 455/41.2 |
| 2014/0304700 A1 | 10/2014 | Kim et al. |
| 2015/0006870 A1 | 1/2015 | Switzer et al. |
| 2015/0065049 A1 | 3/2015 | Heo et al. |
| 2015/0081062 A1 | 3/2015 | Fyfe et al. |
| 2015/0081763 A1 * | 3/2015 | Sipola ..................... A61B 5/00 709/203 |
| 2015/0348380 A1 | 12/2015 | Takayama |
| 2016/0021192 A1 * | 1/2016 | Passichenko ....... H04L 63/0428 713/168 |
| 2016/0029202 A1 * | 1/2016 | Leno .................. H04L 65/1006 455/405 |
| 2016/0037563 A1 * | 2/2016 | Debates .............. H04L 61/6022 455/41.2 |
| 2016/0309286 A1 | 10/2016 | Son et al. |
| 2016/0353503 A1 | 12/2016 | Folske et al. |
| 2017/0045928 A1 | 2/2017 | Ishikawa et al. |
| 2017/0181628 A1 | 6/2017 | Burnette et al. |

OTHER PUBLICATIONS

Sep. 12, 2016—(WO) ISR & WO—App. No. PCT/US16/034746.
2016 Wep 6—(WO) WO & ISR—App. No. PCT/US16/034041.
Jan. 22, 2019—(EP) ESR—App. No. 16804141.6.

* cited by examiner

TRANSMITTING ATHLETIC DATA USING NON-CONNECTED STATE OF DISCOVERY SIGNAL

CROSS-REFERENCE TO RELATED APPLICATIONS

This application claims priority to U.S. Provisional Patent Application No. 62/167,943, filed on May 29, 2015, which is expressly incorporated herein by reference in its entirety for any and all non-limiting purposes.

BACKGROUND

Certain devices, such as many modern fitness devices, are limited in terms of their on-board UIs. Indeed, with the miniaturization of fitness devices, display devices and/or other feedback mechanisms, such as LEDs or tactile input/output devices have been eliminated or made to be more rudimentary than prior models or earlier fitness devices. For example, earlier fitness devices may have included an appendage worn device that was comparable to a bulky wrist-worn watch, however, bracelets, arm bands and other less bulky or obtrusive devices may have minimal UIs and/or feedback mechanisms in terms of one or more of size, quantity, and/or complexity.

Often times, mobile devices, which may be wirelessly linked with said fitness devices may serve as a UI or feedback mechanism. Unfortunately, many users often do not want to have physical possession of their mobile devices while participating in athletic activities, and if so, accessing and utilizing an "app" or other remote software implementations can be time-consuming and burdensome during the athletic activity.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
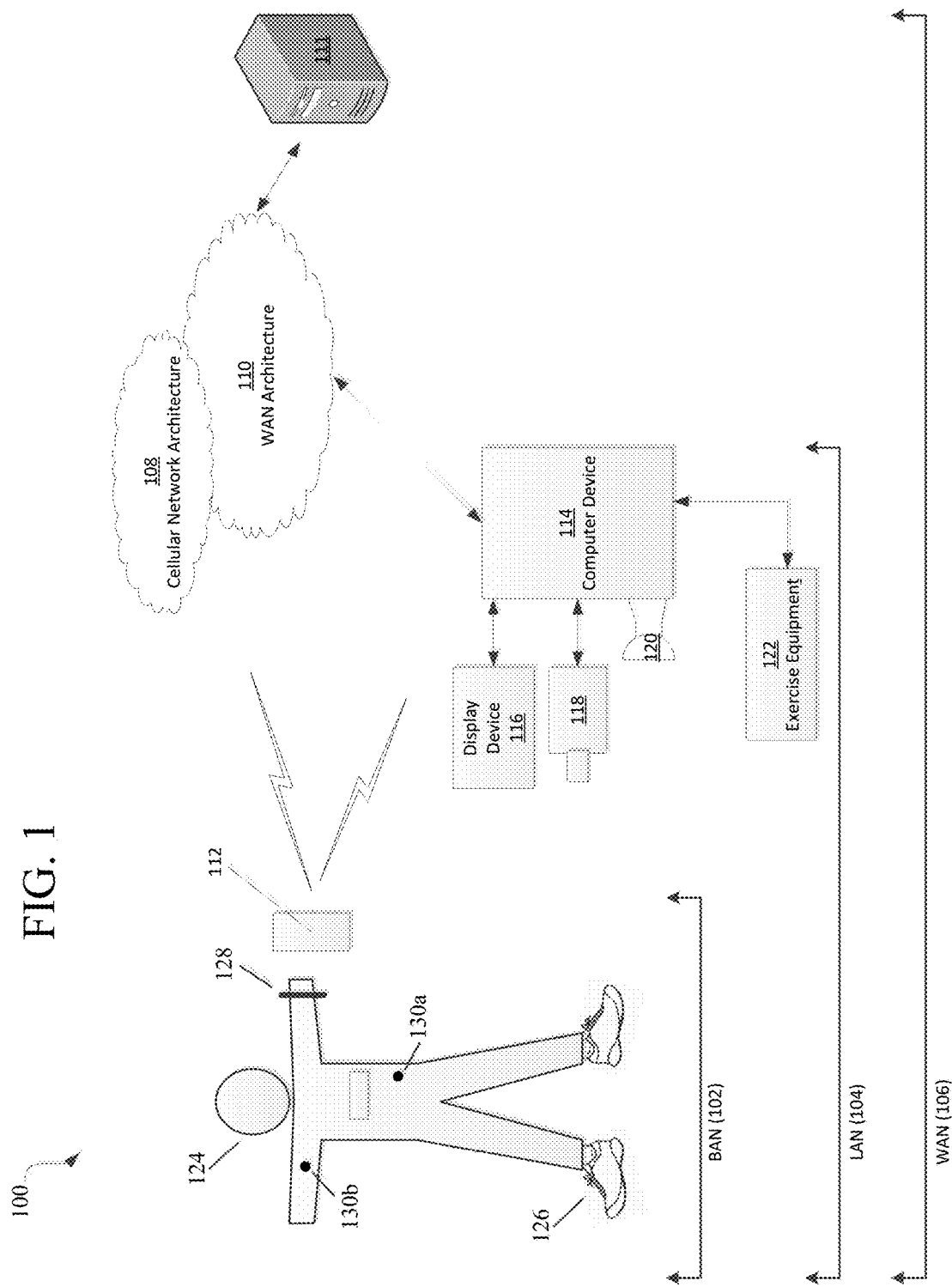
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
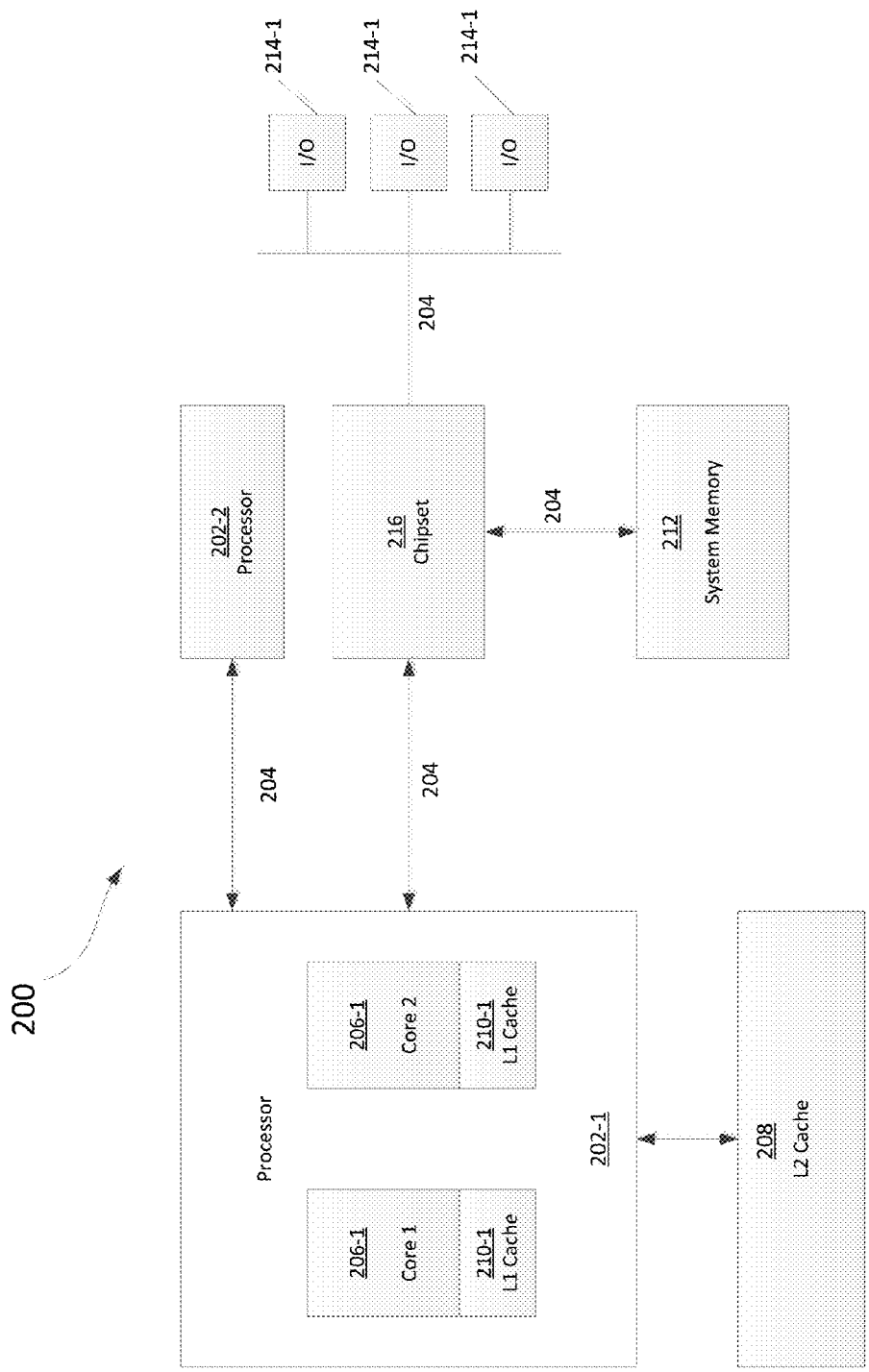
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 120 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 118 and/or sensor 120 may comprise one or more thermal imaging devices. In one embodiment, image-capturing device 118 and/or sensor 120 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
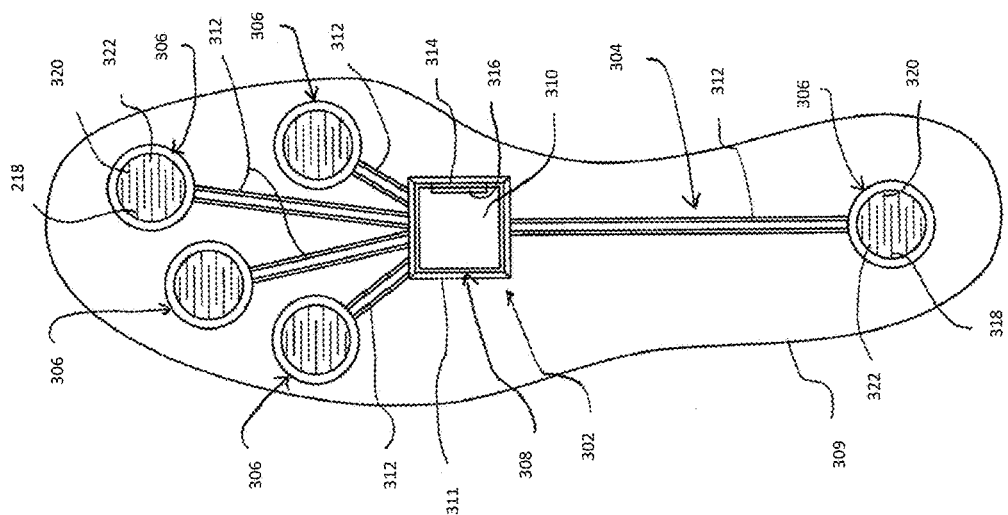
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 218, 320 and a force-sensitive resistive material 322 disposed between the electrodes 218, 320 to electrically connect the electrodes 218, 320 together. When pressure is applied to the force-sensitive material 322, the resistivity and/or conductivity of the force-sensitive material 322 changes, which changes the electrical potential between the electrodes 218, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 218, 320. In some circumstances, this type of force-sensitive resistive behavior may be described as "contact-based resistance."

ii. Wrist-Worn Device

Figure 4:
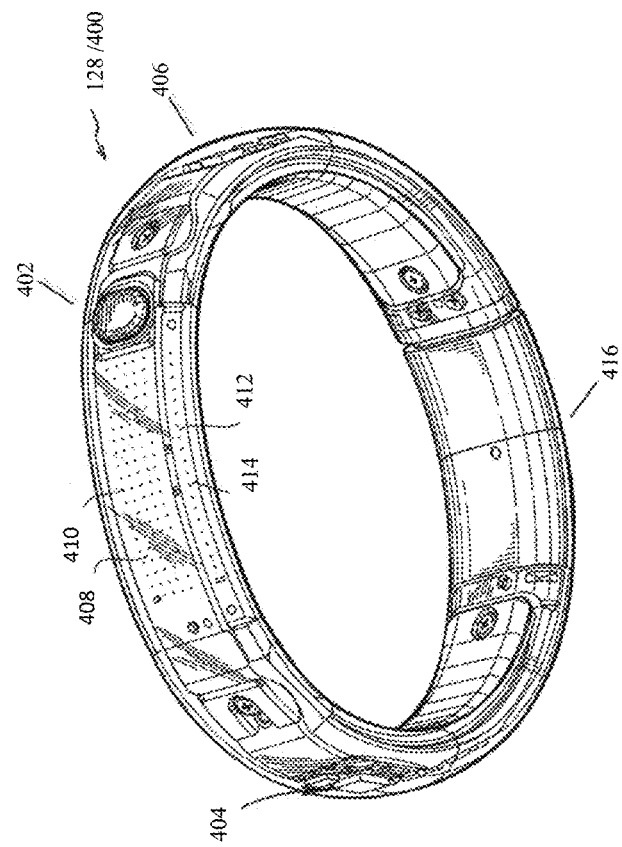
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
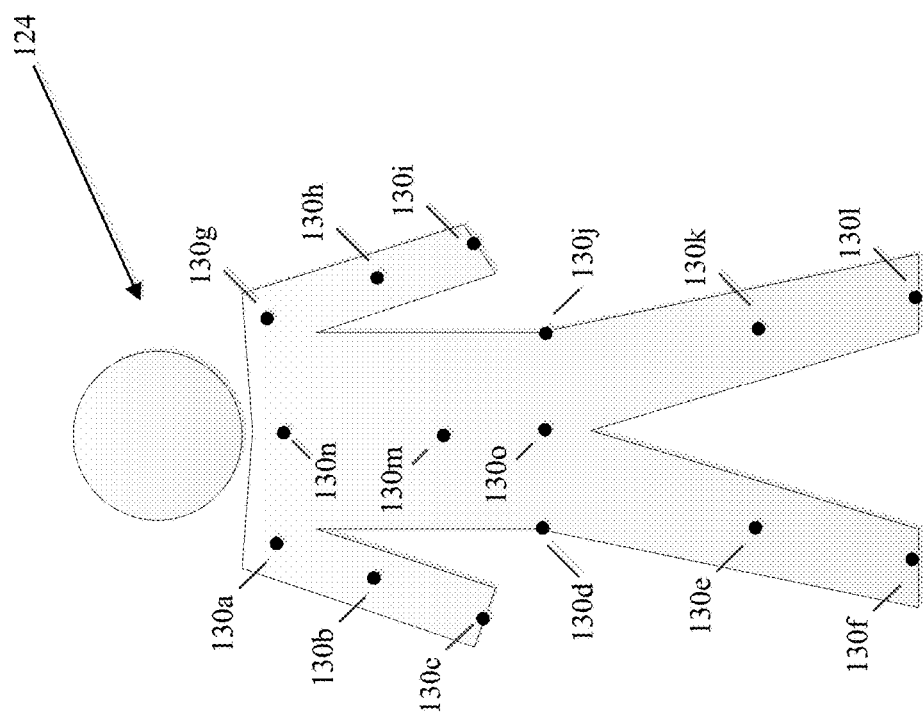
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 130n may be located at about the sternum of user 124. Likewise, sensor location 130o may be located approximate to the navel of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

Transmitting Athletic Data

Aspects of innovations disclosed herein relate to using an altered discovery and/or authentication beacon to transmit sensed data. The sensed data may comprise or consist of athletic data. In one embodiment, the discovery and/or authentication beacon is configured to link or pair two devices and not transmit sensed data, however, is altered to permit the transmission of substantially real-time identification and/or athletic data without a second device that receives the beacon to be linked or otherwise paired.

Further aspects of this disclosure relate to utilizing a discovery beacon in relation to social athletic functions. In certain embodiments, embodiments may utilize a discovery authentication signal to transmit athletic data such that athletic data from a plurality of similar devices may be used. In certain embodiments, the discovery authentication signal may be used while the fitness device is a "non-connected" state, such as the device is not successfully paired with a local device while transmitting athletic data utilizing the discovery authentication signal. In yet, another embodiment, the fitness device may be operatively connected to and actively paired with at least one device, however, is still transmitting the discovery authentication signal that is detected by a second device. As such, with respect to the second device, the wireless signal comprising the discovery authentication signal is essentially performing non-connected advertising. For example, in one embodiment, a fitness device may be actively paired to a user's mobile device, such as a mobile phone, while also transmitting out a discovery authentication signal. In certain embodiments, one or more portions of the discovery authentication signal may be altered, augments or otherwise changed.

In one embodiment, a fitness device, such as one worn or in operative communication with a user, may be wirelessly connected to a mobile device, such as a phone to transmit and/or receive electronic information, however, still advertise out the beacon to other devices. In various embodiments, this may solve problems relating to special hardware being required for hosting multiple connections simultaneously. In various embodiments, a third party may determine which of a plurality of advertised beacons to display or transmit to one or more individuals. For example, a manager of a leaderboard, a trainer, coach, or other individual may possess some control on what advertised data he/she shows and how. Thus, certain embodiments relate to a unique implementation of a non-connectable advertising data transfer system and a system of utilizing data by a third person or system.

Aspects of this disclosure relate to systems and methods that allow multiple users, which may be physically proximate to each other, e.g., in a work out class, school, defined area, etc. or remote (e.g., such as virtually connected via a wired or wireless video capable link or wireless link that allows the transfer of information), to socially engage other user's during the performance of athletic activity. In certain embodiments, at least two of the users may have a fitness device capable of measuring athletic activities. One or more of the fitness devices may utilize one or more of the sensors disclosed herein. One or more of the devices may be capable of communicating over a wireless or contactless communication interface, such as an interface for Wi-Fi, Bluetooth, near-field communication, RFID, Bluetooth Low Energy, Zigbee, or other wireless communication technique, or an interface for infrared or other optical communication technique. The fitness devices may be configured to utilize a specific transmission protocol that requires pairing or otherwise authenticating at least one device in the communication pathway (e.g., Bluetooth). The fitness device(s) may be configured to transmit a discovery beacon that is configured to transmit the identification of the fitness device configured to be received by a second device, such that the beacon allows the second device detect the presence of the fitness device. In one embodiment, a specific make and model of a fitness device may have a universal beacon. For example, a $2^{nd}$ generation Nike Fuelband may transmit an authentication discovery beacon consisting of "FB2" whereas a first generation Nike Fuelband may transmit a beacon consisting of "FB1". Those skilled in the art will realize that any identification that may be used in the authentication/discovery of the fitness device may be utilized. As such, any alphanumeric string, such as 033007CRG, may be utilized within the scope of this disclosure. A second manufacturer of a fitness device may use one or more beacons for distributed fitness devices. Again, such beacons may be configured to allow the discovery/identification of the fitness device to a second device for pairing purposes. In certain embodiments, the sole function of the function of the beacon is to allow the discovery/identification of the fitness device for linking or pairing purposes.

Proximity Pairing Examples

As indicated above, aspects of this disclosure relate to utilizing a discovery beacon in relation to social athletic functions. In certain embodiments, embodiments may utilize a discovery authentication signal to transmit athletic data such that athletic data from a plurality of similar devices may be used. In certain embodiments, the discovery authentication signal may be used while the fitness device is a "non-connected" state, such as the device is not successfully paired with a local device while transmitting athletic data utilizing the discovery authentication signal. In yet, another embodiment, the fitness device may be operatively connected to and actively paired with at least one device, however, is still transmitting the discovery authentication signal that is detected by a second device. As such, with respect to the second device, the wireless signal comprising the discovery authentication signal is essentially performing non-connected advertising. For example, in one embodiment, a fitness device may be actively paired to a user's mobile device, such as a mobile phone, while also transmitting out a discovery authentication signal. In certain embodiments, one or more portions of the discovery authentication signal may be altered, augments or otherwise changed.

In further embodiments, the discovery authentication signal comprises a unique identifying signal may be alternatively utilized, either in conjunction with or instead of a common identifying signal. In one embodiment, which is described below, a common string may be replaced or altered to provide a unique string. In one embodiment, a signal may comprise a common identifying string (e.g., FB2) as well as a unique global identifier (e.g., 090310SPG vs. 110775SPG). An example of a unique global identifier may be similar or the same as the 48-bit unique identifier imprinted for each Bluetooth radio.

Systems and methods may be utilized to use obtain electronic information and/or identify specific devices among a plurality of like devices, such as devices that have a common default discovery authentication signal. For example, one or more users in a class may be utilizing the same make and model of a fitness device. The fitness devices may have limited user interfaces. For example, certain devices may only have a single light or tactile ability. Those with limited UI or feedback abilities generally may present a challenge when attempting to identify a single device in the presence of other similar or identical fitness devices.

In accordance with one embodiment, a known discovery token for an un-imprinted device may be obtained. The discovery token may be stored in one or more computer-readable mediums, including those shown and described in relation to FIGS. 1-4. A first device, such as a mobile device may comprise a processor and a non-transitory computer-readable medium including computer-executable instructions causes the processor to perform one or more routines, processes or steps. In one embodiment, an "app" may quickly identify un-imprinted fitness devices within a proximity. In one embodiment, only fitness devices having a predefined name may be presented to the user of the device. In further embodiments, imprinted devices may be filtered out. In accordance with one embodiment, upon imprinting, the discovery token will be changed to a value unique to the specific device and/or user of the device.

Figure 6:
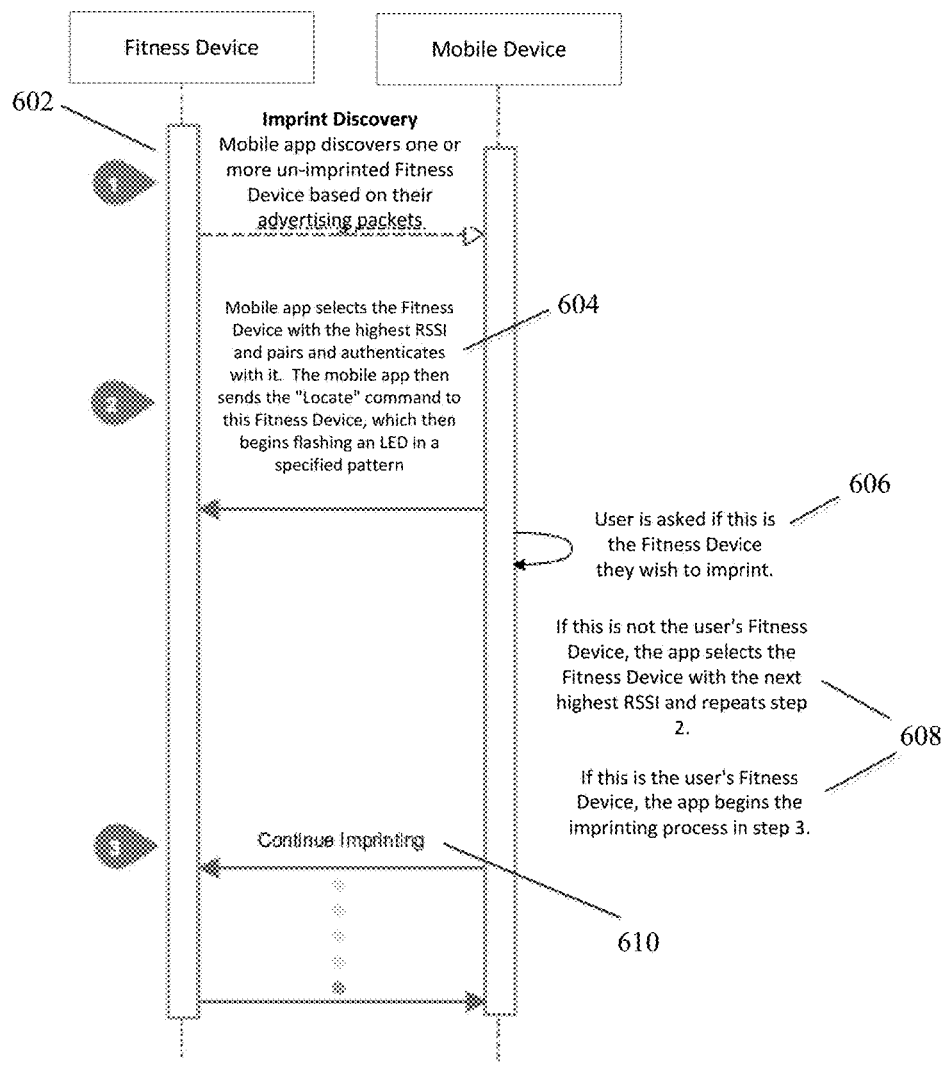
FIG. 6 shows an example flow of proximity pairing one of a plurality of fitness devices according to one example embodiment disclosed herein.

In one embodiment, authentication and/or a pairing process may occur, either prior to or as part of an imprinting process. FIG. 6 is a flowchart of one exemplary embodiment that may be used to implement proximity pairing in accordance with one or more implementations according to various embodiments in which information and actions between "Fitness Device" and a "Mobile Device" is provided. Those skilled in the art will appreciate that "mobile device" is merely an example, and as such any device comprising at least one processor and a memory may be utilized in accordance with this disclosure. Further, in certain embodiments, a mobile device may comprise a proximity pairing module, which may comprise software and/or hardware components. In one embodiment, a mobile device is configured to include computer-executable instructions that when executed initiate an "app" of set of instructions that, when executed by a processor, perform one or more of the actions or transfer of information discussed in accordance with FIG. 6 (as well as others).

In accordance with one embodiment, one or more un-imprinted fitness devices may be detected. In one embodiment, the fitness devices may be discovered via an advertising beacon (e.g. see 602). The advertising beacon may be configured to serve as a discovery authentication beacon. In one embodiment, the beacon may consist of a discovery authentication beacon. Computer-executable instructions may be executed to cause a UI, such instructions on a non-transitory medium on the mobile device, to instruct a user to move their fitness device within a set proximity to the device. In one embodiment, the distance may be less than 1 ft. In yet another embodiment, it may be as close as the user can physically space the two fitness device to the device.

A selection process configured to select the intended fitness device may occur (see, e.g., 604). In one possible implementation, the app (or module on the mobile device) may then filter the list of detected devices meeting the criteria (e.g., un-imprinted devices) such as by RSSI (Received Signal Strength Indication) and build an internal list based on those fitness devices having a strong signal. This threshold may be set by one or more criteria, and in certain embodiments, user defined. In certain embodiments, once an internal list of un-imprinted devices is created, it may attempt connection with the fitness device on the listing associated with the highest RSSI. Upon connection, a command may be transmitted to the connected fitness device to cause it to output a signal, such as via one of its (albeit limited) UI or feedback mechanisms, such as via flashing light, making a sound or a vibration. In one embodiment, this may be referred to as a "Locate Device" command. In one embodiment, the Locate Device command may cause blinking of an LED in a particular pattern. The app may then ask the user if their device is blinking. (see, e.g., 606).

Various embodiments require or otherwise permit the receipt of a user input relating to the state of the fitness device (see, e.g., 608). For example, if a user input is indicative of the affirmative (e.g., lights are blinking at the predefined rate or pattern), then imprinting may proceed in certain embodiments. (see, e.g., 610). If a user input is indicative of a negative response (e.g., the user provides an input indicating that the specific device is not outputting a specific output signal), the app may cease instructions configured to blink the current device, disconnect and connect to a device with the next highest RSSI and ask the user if their device is now blinking. This process may be repeated until a user input is in the affirmative and/or the list of devices is exhausted.

Imprinting Fitness Device Examples

Figure 7:
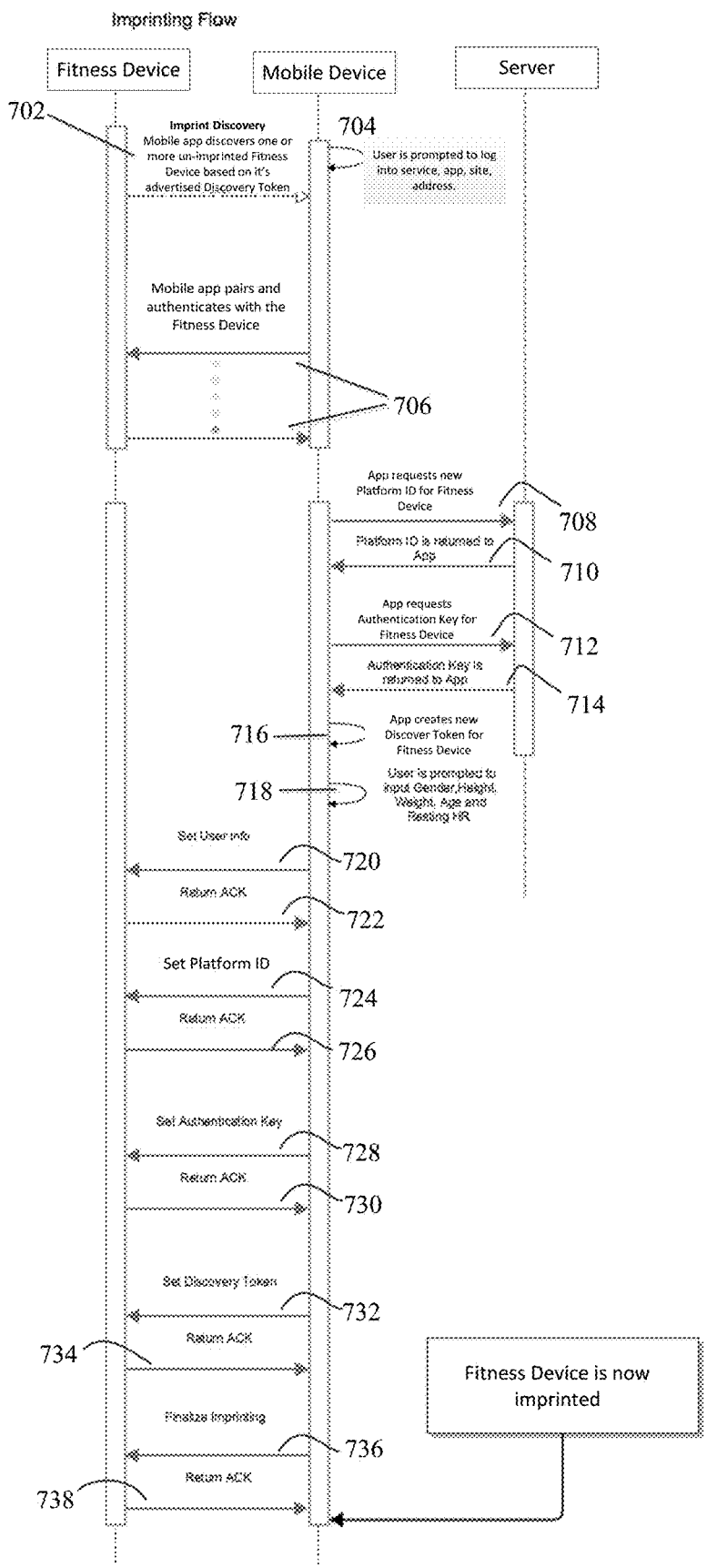
FIG. 7 shows an example flow of imprinting a fitness device according to one example embodiment disclosed herein.

In one embodiment, imprinting may occur. FIG. 7 is a flowchart of one exemplary embodiment that may be used to implement an imprinting protocol in accordance with one or more implementations according to various embodiments in which information and actions between a "Fitness Device", a "Mobile Device" and a "Server" is provided. As discussed above with reference to FIG. 6, those skilled in the art will appreciate that "mobile device" is merely an example, and as such any device comprising at least one processor and a memory may be utilized in accordance with this disclosure. Further, in certain embodiments, a mobile device may comprise a proximity pairing module, which may comprise software and/or hardware components. In one embodiment, a mobile device is configured to include computer-executable instructions that when executed initiate an "app" of set of instructions that, when executed by a processor, perform one or more of the actions or transfer of information discussed in accordance with FIG. 7 (as well as others). Likewise, reference to a "Server" may include any proximate or remote computing device having at least a processor and a non-transitory computer-readable medium.

In accordance with one embodiment, one or more unimprinted fitness devices may be detected. In one embodiment, the fitness devices may be discovered via an advertising beacon (e.g. see 702, which in certain embodiments may be identical or comprise one or more processes similar to 602). The advertising beacon may be configured to serve as a discovery authentication beacon. In one embodiment, the beacon may consist of a discovery authentication beacon. Computer-executable instructions may be executed to cause a UI, such instructions on a non-transitory medium on the mobile device, to instruct a user to log into an app, service, or virtual address (such as for example, a URL), such as shown graphically with reference 704 of FIG. 7. Either based upon the reception of a signal, such as via 702 and/or the user successfully being granted entry to the service, system, app, site, and/or address, such as represented by reference 704 of FIG. 7, the mobile device and the fitness device may be paired (e.g., see reference 706).

In certain embodiments, the Mobile Device (or a module operating in association with the Mobile Device) may transmit a request for a new identification from the site, service, site, address, etc. For example, it may be a "Platform ID". (e.g., see reference 708). It may be requested from the "Server". The Server, in turn, may provide the requested ID (e.g., the "Platform" ID) to the device (e.g., reference 710). The mobile device may request an authentication key for the fitness device (e.g., reference 712), which may be transmitted as part of illustrated process 714.

The mobile device, or portions thereof, may then create a new Discovery Token or other beacon that is different than the Discovery Token or beacon of 702 (e.g., see, arrow 716). The creation of the Discovery Token/beacon may be based on the user credentials or information known to the service, site, app, address, etc. of reference 704. The creation of the Token/beacon may be performed entirely without the Fitness Device.

The user may be prompted, such as with a UI provided on the Mobile Device, to provide physiological, athletic, and/or demographic information. In one embodiment, the user may be prompted to provide one or all of: gender, height, weight, and their estimated or known resting heart rate. (e.g., see arrow 718). This and/or other user information may be transmitted to the Fitness Device (e.g., arrow 720), which may be followed by an acknowledgement signal (e.g., ACK message of arrow 722). The ID (e.g., Platform ID of 710) may also be transmitted to the Fitness Device (e.g., arrow 724), and an acknowledgement message may be received responsive thereto (e.g., arrow 726). An authentication key (e.g., Authentication Key of 712/714) may be transmitted to the Fitness Device (e.g., arrow 728), which may be followed by an acknowledgement signal (e.g., 730). The Discovery Token (such as the one created by the Mobile Device in arrow 716) may be set in the Fitness Device (see, e.g., arrow 732), which may be acknowledged with a message (e.g., arrow 734). Setting the Discovery Token at arrow 732 may completely erase or otherwise render unusable the prior Discovery Token on the Fitness Device, yet in other embodiments, it may be temporary. In one embodiment, the Discovery Token set at arrow 732 may auto-expire upon lapsing of time and/or meeting of one or more other conditions. In yet another embodiment, a user input may be required to remove or otherwise replace the Discovery Token of 732. In further embodiments, imprinting may be finalized (e.g., arrow 736), which may be acknowledged in a message (see, e.g., arrow 738), thus resulting in the Fitness Device being imprinted.

In certain embodiments, it may be critical that an authentication key and a discovery token are committed to non-volatile memory nearly simultaneously, such as within a finite threshold time frame. If there is any disruption in communication that results in only one of these values being correctly written to memory, the imprinting process may have presumed to have failed. At this point, the Fitness Device may be in one of two error states. If the Advertising Token was written but the Authentication key was not, the fitness device may incorrectly advertise and be incorrectly recognized as an imprinted device. Thus, the app may attempt to authenticate with the user's authentication key, and authentication will fail. If the Authentication key was written and the Discovery token was not, the fitness device may appear as an un-imprinted device. The app may attempt to connect and authenticate using the default authentication key. The fitness device may use the written user's authentication key during the process and authentication will fail.

Systems and methods may mitigate imprint failure according to novel implementations. In one embodiment, to minimize the exposure to this issue, a Discovery Token and Authentication Key may be held in volatile memory until acknowledgement that the imprinting is successful. In one embodiment, a "Finalize Imprinting" command is received. Upon receiving the Finalize Imprinting command, firmware may write the Discovery Token and Authentication keys to non-volatile memory. Firmware may then return an ACK for the received command.

What is claimed is:

1. An electronic device comprising:
   a processor;
   a transceiver configured to wirelessly receive electronic information via a direct connection with a second electronic device using a transmission protocol that can perform at least one of:
      transmitting an advertising beacon that identifies the transceiver as associated with the electronic device; or
      receiving an advertising beacon that identifies a transceiver as associated with a second electronic device, wherein identification of an advertising beacon is utilized in an establishment of a direct connection between the electronic device and the second electronic device; and
   a computer-readable medium comprising computer-executable instructions that when executed by the processor perform at least:
      receive a plurality of advertising beacons from a plurality of electronic devices without establishing a direct connection with any of the plurality of electronic devices;

determine that each electronic device, of the plurality of electronic devices, is available for pairing based on a determination that each electronic device, of the plurality of electronic devices, is a first type of fitness device that utilizes a non-unique identifying string in its advertising beacon;

generate a first list of devices, the first list of devices comprising the plurality of electronic devices;

filter the first list of devices to generate a second list of devices, wherein the filtering comprises determining, from the plurality of electronic devices, a sub-set of electronic devices that each have a signal strength above a threshold value, and wherein the second list of devices comprises at least the second electronic device and a third electronic device;

select, from the second electronic device and the third electronic device, and based on a first signal strength associated with the second electronic device and a second signal strength associated with the third electronic device, a pairing device;

connect to the pairing device using a first communication protocol;

transmit a command to the pairing device, the command configured to provide an output on the pairing device;

responsive to transmitting the command, receive a user input indicating that the pairing device is not outputting a specific output signal;

responsive to the user input indicating that the pairing device is not outputting the specific output signal, disconnect from the pairing device and select, from the second list of devices, a second pairing device; and connect to the second pairing device.

2. The electronic device of claim 1, wherein the first signal strength and second signal strength are determined based on RSSI packets.

3. The electronic device of claim 1, wherein the command transmitted to the pairing device is configured to cause an illumination of a light source on the pairing device.

4. The electronic device of claim 1, wherein the command transmitted to the pairing device configured to provide an output on the pairing device comprises transmitting a command configured to alter a graphical user interface of the pairing device.

5. The electronic device of claim 1, wherein the computer-readable medium further comprises computer-executable instructions that when executed, cause the processor to at least:

receive a unique string from a user providing a user input into a user interface; and transmit the unique string to the pairing device.

6. The electronic device of claim 1, wherein the computer-readable medium further comprises computer-executable instructions that when executed, cause the processor to at least:

determine a unique string comprising information derived from an athletic attribute of a user associated with the pairing device; and transmit the unique string to the pairing device.

7. The electronic device of claim 1, wherein the computer-readable medium further comprises computer-executable instructions that when executed, cause the processor to at least:

during imprinting, request a platform identification for the pairing device;

receive the platform identification, and in response request an authentication key.

8. The electronic device of claim 7, wherein the computer-readable medium further comprises computer-executable instructions that when executed, cause the processor to at least:

during imprinting, create a discovery token for the pairing device.

9. The electronic device of claim 1, wherein the computer-readable medium further comprises computer-executable instructions that when executed, cause the processor to at least:

prior to finalizing imprinting, request demographic information from a user.

10. A method comprising:

receiving, from a plurality of electronic devices, a plurality of advertising beacons each identifying a transceiver associated with a respective electronic device of the plurality of electronic devices, without establishing a direct connection with any of the plurality of electronic devices;

determining that each electronic device, of the plurality of electronic devices, is available for pairing based on a determination that each electronic device, of the plurality of electronic devices, is a first type of fitness device that utilize a non-unique identifying string in its advertising beacon;

generating a first list of devices comprising the plurality of electronic devices;

filtering the first list of devices to generate a second list of devices, wherein the filtering comprises determining, from the plurality of electronic devices, a sub-set of electronic devices that each have a signal strength above a threshold value, and wherein the second list of devices comprises at least a first electronic device and a second electronic device;

selecting, from the first electronic device and the second electronic device, and based on a first signal strength associated with the first electronic device and a second signal strength associated with the second electronic device, a pairing device;

connecting to the pairing device using a first communication protocol;

transmitting a command to the pairing device, the command configured to provide an output on the pairing device;

responsive to transmitting the command, receiving a user input indicating that the pairing device is not outputting a specific output signal;

responsive to the user input indicating that the pairing device is not outputting the specific output signal, disconnecting from the pairing device and selecting, from the second list of devices, a second pairing device; and connecting to the second pairing device.

11. The method of claim 10, wherein the first signal strength and second signal strength are determined based on RSSI packets.

12. The method of claim 10, wherein the command transmitted to the pairing device is configured to cause an illumination of a light source on the pairing device.

13. The method of claim 10, wherein the command transmitted to the pairing device configured to provide an output on the pairing device comprises transmitting a command configured to alter a graphical user interface of the pairing device.

14. The method of claim 10, further comprising:
receiving a unique string from a user providing a user input into a user interface; and
transmitting the unique string to the pairing device.

15. The method of claim 10, further comprising:
determining a unique string comprising information derived from an athletic attribute of a user associated with the pairing device; and
transmitting the unique string to the pairing device.

16. The method of claim 10, further comprising:
requesting, during imprinting, a platform identification for the pairing device;
receiving the platform identification; and
requesting an authentication key in response to receiving the platform identification.

17. The method of claim 10, further comprising:
creating, during imprinting, a discovery token for the pairing device.

18. The method of claim 10, further comprising:
requesting demographic information from a user.

* * * * *